United States Patent [19]

Egozy et al.

[11] Patent Number: 5,272,091
[45] Date of Patent: Dec. 21, 1993

[54] WATER PURIFICATION METHOD AND APPARATUS

[75] Inventors: Yair Egozy, Lexington; Adam D. Foley, Westwood; Gary A. O'Neill, Tyngsborough, all of Mass.

[73] Assignee: Millipore Corporation, Bedford, Mass.

[21] Appl. No.: 920,604

[22] Filed: Jul. 27, 1992

[51] Int. Cl.$^5$ ............................................. G01N 27/06
[52] U.S. Cl. ..................................... 436/146; 422/68.1; 422/78; 422/82.02; 436/145
[58] Field of Search ............ 422/37, 68.1, 82.05, 422/37, 78, 80, 82.12, 186.3, 82.02; 436/146, 145; 210/96.1, 758, 143, 748, 424, 746, 652, 662

[56] References Cited

U.S. PATENT DOCUMENTS

| | | | |
|---|---|---|---|
| 3,607,071 | 9/1971 | Staffin et al. | 422/78 |
| 4,000,065 | 12/1976 | Ladha et al. | 210/652 |
| 4,280,912 | 7/1981 | Berry, III et al. | 210/662 |
| 4,595,498 | 6/1986 | Cohen et al. | 210/195.1 |
| 4,626,413 | 12/1986 | Blades et al. | 422/78 |
| 4,666,860 | 5/1987 | Blades et al. | 436/146 |
| 4,775,634 | 10/1988 | Sienkiewicz | 436/146 |
| 4,787,980 | 11/1988 | Ackermann | 210/652 |
| 4,944,875 | 7/1990 | Gaignet | 210/232 |
| 5,047,212 | 9/1991 | Blades et al. | 436/146 |
| 5,073,268 | 12/1991 | Saito et al. | 210/748 |
| 5,147,605 | 9/1992 | Tatsuno et al. | 422/37 |

FOREIGN PATENT DOCUMENTS

| | | |
|---|---|---|
| 8909536 | 10/1989 | European Pat. Off. . |
| 2500430 | 8/1982 | France . |
| 261585 | 12/1985 | Japan . |
| 1-236986 | 9/1989 | Japan . |
| 3-118889 | 5/1991 | Japan . |
| WO 91/06848 | 11/1990 | PCT Int'l Appl. . |

OTHER PUBLICATIONS

Sandler, Henry et al., "Practical Process Engineering", p. 91, McGraw Hill Book Company, N.Y., 1987.
Kohout, R., "Ultrapure Water and Reverse Osmosis", Solid State Technology, vol. 17, No. 6, pp. 60-65, 1974 (Jun.).

*Primary Examiner*—James C. Housel
*Assistant Examiner*—Ramon Torres
*Attorney, Agent, or Firm*—Hamilton, Brook, Smith & Reynolds

[57] ABSTRACT

A method and apparatus predict the organic carbon content of water discharged from a water purification system. Water is directed from a water source across, for example, a source of ultraviolet light of the water purification system under substantially steady-state conditions. A reference mode is established, whereby a reference-mode resistivity change is determined. A purification-mode is then established, whereby a purification mode resistivity change is measured. The reference-mode resistivity change and the purification-mode resistivity change are then combined to obtain a purified value which is associated with the carbon content of water discharged from the water purification system, thereby predicting the carbon content of water discharged from the water purification system.

25 Claims, 4 Drawing Sheets

WATER PURIFICATION METHOD AND APPARATUS

BACKGROUND OF THE INVENTION

Many industrial applications of water require the use of ultrapure water, which is water that has a very low organic carbon content, i.e. less than about twenty-five parts per billion. For example, oxidation of substrates during manufacture of integrated electronic circuits can be deleteriously affected by the presence of organic deposits on the substrate surface. Ultrapure water is often employed to dissolve organic deposits from substrate surfaces prior to oxidation. Other typical applications for which ultrapure water is employed include the manufacture of medical devices, chemicals, and analytical laboratory applications.

Ultrapure water is typically prepared by methods which include, for example, filtration, ion exchange and exposure to ultraviolet radiation. However, the ability of a water purification system to reduce the organic carbon content of water to acceptable levels varies according to the conditions of filtration, such as the temperature and flow rate of the water through the purification system. Also, the effectiveness of purification is generally dependent, at least in part, upon the quantity and type of organic contaminants within the water being purified. Consequently, the organic carbon content of ultrapure water can vary significantly during minor changes in the operating conditions of purification.

One attempt to monitor the organic carbon content of ultrapure water is based on oxidation of organic carbon to form carbon dioxide, such as by exposure of the water to ultraviolet light. For example, Patent Cooperation Treaty (PCT) patent application PCT/JP90/01434, by Nihon Millipore Kogyo Kabushiki Kaisha, published May 16, 1991 as WO91/06848, discloses a method and apparatus for monitoring the organic carbon content of ultrapure water by monitoring the difference in electrical resistivity of the water across an ultraviolet light during purification. The value of the organic carbon content of water discharged from the water purification system is presumed, based on a known organic carbon content of the water prior to exposure to ultraviolet light and on an observed drop in resistivity across the light. However, other factors may affect the carbon content and thus can cause an error in the presumed value. Examples of such factors include changes in the temperature and flow rate of the water in the purification system, the nature of the organic carbon content in the water, and aging of components in the purification system. Another limitation of this prior art system involves the fact that oxidation products emanating from the ultraviolet light are not always the same. It is known that a particular resistivity change could be produced by different levels of different oxidation products. For example, if carboxylic acids are formed as an oxidation product, the resulting resistivity change could be the same as that resistivity change produced by a different level of carbon dioxide, yet the measured total organic carbon content of these two oxidation products could be different. Thus, this system does not take into account variances of the oxidation products produced. Due to the diversity of organic compounds found in feed waters, this is an important factor to consider in the design of a water purification system.

Also, known apparatus for estimating the total organic carbon content can be cumbersome when used in conjunction with water purification systems. An example of an apparatus for estimating the total organic carbon content of ultrapure water is disclosed in U.S. Pat. No. 5,047,212, issued to Blades et al. (hereinafter "Blades et al."). Blades et al. disclose exposure of a sample of ultrapure water to ultraviolet light and recording of the electrical resistivity of the water over time during exposure to the ultraviolet light. However, the system and method disclosed by Blades et al., is time consuming. For example, a single estimate of the organic carbon content of a sample of ultrapure water withdrawn from a water purification system can require about one-half hour.

Further, water purification systems are typically operated on a continuous basis. Also, the conditions of the water purification system and of the water directed into the system can vary significantly during analysis of the sample withdrawn from the system. Consequently, the estimated organic carbon content value obtained by Blades et al., can be obsolete before the value can be reported. As a result, monitoring of the water purification system can be employed only when steady-state conditions of the system can be assured over extended periods of time.

Therefore, a need exists for a method and apparatus for predicting and monitoring the organic carbon content of water discharged from a water purification system which overcome or minimize the above-referenced problems.

SUMMARY OF THE INVENTION

The present invention relates to a method and apparatus for predicting and monitoring the organic carbon content of water discharged from a water purification system.

The method for predicting the organic carbon content of water discharged from a water purification system includes directing water from a water source through an oxidation means of the water purification system under substantially steady-state conditions. A reference mode is established by exposing water to the oxidation means for a sufficient number of significantly different time periods to determine a reference-mode resistivity change. A purification mode is established, wherein the water is directed through the oxidation means under the steady-state conditions previously mentioned. A purification-mode resistivity change of the water is measured across the oxidation means while the water purification system is at the steady-state conditions. The reference-mode resistivity change is combined with the purification-mode resistivity change to obtain a purified value which is associated with the carbon content of water discharged from the water purification system, thereby predicting the carbon content of water discharged from the water purification system.

The method for monitoring the organic carbon content of water discharged from a water purification system includes directing the water from a water source through an oxidation means of the water purification system under substantially steady-state conditions. A reference mode is established by exposing water to oxidation means for a sufficient number of significantly different time periods to determine a reference-mode resistivity change. A purification mode is established, wherein the water is directed through the oxidation means under the steady-state conditions previously mentioned. A purification-mode resistivity change of the water is measured across the oxidation means while the water purification system is at the steady state conditions, whereby the organic carbon content of water discharged from the water purification system in the purification mode can be verified, following significant variation of the purification-mode resistivity change. The organic carbon content of the discharged water is verified by redirecting water through the water purification system in the reference mode to obtain a second reference-mode resistivity change which can be combined with the purification-mode resistivity change as measured following the previously-mentioned significant variation. The measured resistivity changes are combined to predict a new value of the carbon content of the water discharged from the water purification system, thereby monitoring the organic carbon content of water discharged from the water purification system.

The apparatus for predicting the organic carbon content of water discharged from a water purification system includes a three-way valve having an inlet, a first outlet, and a second outlet. A first resistivity cell is in fluid communication with the inlet of the three-way valve. An oxidation means exposes water directed through the purification system to conditions sufficient to reduce the organic carbon content of the water to a purified value. The oxidation means includes an inlet, in fluid communication with the first outlet of the three-way valve, and an outlet. A second resistivity cell is in fluid communication with the outlet of the oxidation means.

This invention has many advantages. For example, the organic carbon content of water discharged from a water purification system can be predicted in a relatively short period of time without requiring use of expensive peripheral analytical equipment. Further, the purification-mode resistivity change of water across the oxidation means can be monitored continuously while water is purified by the water purification system. Changes in the purification-mode resistivity across the oxidation means, which may reflect a corresponding change in the organic carbon content of water discharged from the water purification system, can be identified essentially instantaneously. The organic carbon content of the purified water can then be verified by converting the water purification system to the reference mode.

DETAILED DESCRIPTION OF THE INVENTION

The features and other details of the apparatus and method of the invention will now be more particularly described with reference to the accompanying drawings and pointed out in the claims. It will be understood that the particular embodiments of the invention are shown by way of illustration and not as limitations of the invention. The principle features of this invention can be employed in various embodiments without departing from the scope of the invention.

Figure 1:
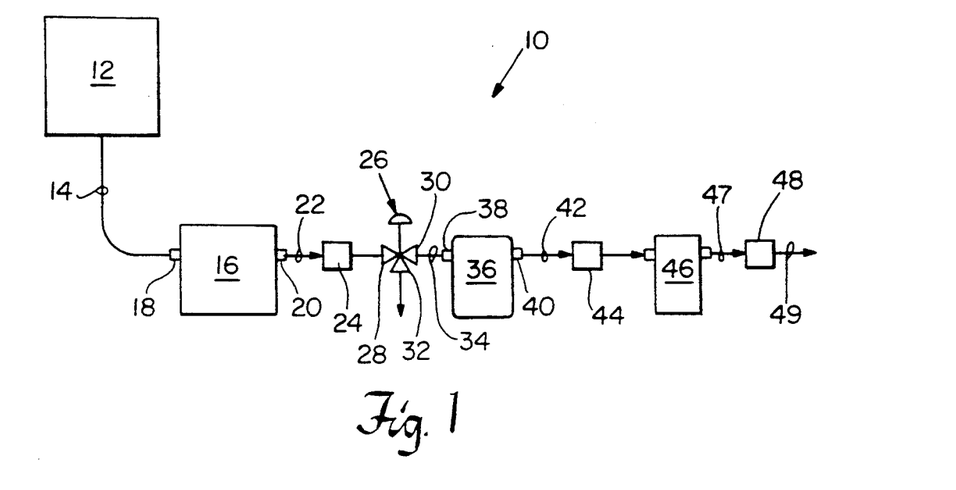
FIG. 1 is a schematic representation of one embodiment of the system of the invention.

In one embodiment of the invention, shown in FIG. 1, water purification system 10 purifies water directed from water source 12. Examples of suitable types of water for purification in water purification system 10 include tap water, deionized water, distilled water, and water treated by reverse osmosis, etc.

Water is directed from water source 12 through conduit 14 to a suitable treatment means, such as treatment means 16. Examples of suitable means by which water is directed from water source 12 through conduit 14 to treatment means 16 include pressurization at water source 12 and gravity feed of water from water source 12.

Treatment means 16 includes inlet 18 and outlet 20. Examples of suitable treatment means are those which include activated carbon and an ion exchange resin components. In one embodiment, the treatment means is a QPAK type purification pack, commercially available from Millipore Corporation, and disclosed in U.S. Pat. No. 4,944,875, issued to Gaignet. Water is directed from conduit 14 through inlet 18 into treatment means 16. Water is treated in treatment means 16 and then discharged through outlet 20. Preferably, in an embodiment wherein the water at water source 12 has been treated by reverse-osmosis, the total organic carbon content (hereinafter "TOC") of water discharged from treatment means 16 is less than about ten parts per billion and has an electrical resistivity of about eighteen megohm-cm.

Water discharged through outlet 20 is directed through conduit 22 and first resistivity cell 24 at conduit 22 to three-way valve 26. Three-way valve 26 includes inlet 28, first outlet 30 and second outlet 32. Conduit 34 extends from first outlet 30 to oxidation means 36.

Three-way valve 26 can be actuated between a first position, wherein water directed through conduit 22 and inlet of three-way valve 26 is conducted through three-way valve and first outlet 30. Three-way valve 26 is in the first position when the water is directed through purification system 10 in a purification mode. In the second position, water directed through inlet 28 of three-way valve 26 is sealed from first outlet 30 and is instead diverted from oxidation means 36 through second outlet 32 of three-way valve 26. Water discharged from three-way valve 26 through second outlet 32 is directed to the effluent or can be recycled to water source 12 by a suitable means, not shown.

The electrical resistivity of water directed through conduit 22 is measured by first resistivity cell 24. Preferably, the electrical resistivity of the water at first resistivity cell 24 is measured continuously. An example of a suitable resistivity cell is a flow-through type resistivity cell.

Oxidation means 36 includes inlet 38 and outlet 40. Inlet 38 is disposed at conduit 34 for receiving fluid from conduit 34 when purification system 10 is in the purification mode. Oxidation means 36 is suitable for producing ionized oxidation products, such as organic acids or carbon dioxide. Preferably, oxidation means 36 produces such oxidation products from the TOC of the water by exposing the water to ultraviolet light. An example of a suitable oxidation means is a mercury vapor type ultraviolet light source. Other types of suitable oxidation means include, for example, introduction of a suitable oxidizing agent, such as hydrogen peroxide, etc. Water in oxidation means 36 is exposed in oxidation means 36 to sufficient conditions to cause a significant portion of the organic carbon to oxidize and thereby form carbon dioxide which becomes dissolved in the water.

"Total organic carbon content," or TOC, as those terms are used herein, means the parts per billion of the water which are carbon atoms associated with organic compounds. Preferably, when purification system 10 is in the purification mode, water is exposed in oxidation means 36 to ultraviolet light at a sufficient intensity and for a sufficient period of time to cause a significant portion of the TOC of the water to become oxidized. Typically, water directed into oxidation means 36 is exposed to ultraviolet light having a wavelength in the range, for example, of between about 185 and 254 nanometers, for a period of time in the range of between about two (2) and one hundred and twenty (120) seconds. In one embodiment, the TOC of water is reduced by oxidation means 36 to an amount which causes resulting polished water to have a TOC which is in the range of between about one (1) and five (5) ppb. It is to be understood, however, that the method and system for monitoring the organic carbon content of water discharged from water purification system 10 is not dependent upon the ability of oxidation means 36 to reduce the TOC of water directed through water purification system 10.

The water is discharged from oxidation means 36 through outlet 40 and conduit 42 which extends from outlet 40. Second resistivity cell 44 is disposed at conduit 42 for measuring the electrical resistivity of water discharged from oxidation means 36. The water is then directed through polisher 46 and line 47 to third resistivity cell 48. Polisher 46 includes ion-exchange resin which removes the ionized oxidation products originating from the oxidation means. The water is then discharged from water purification system 10 through conduit 49, which extends from third resistivity cell 48.

Purification system 10 is operated in the purification mode by directing water from water source 12 through purification system 10 while three-way valve 26 is in the first position. The TOC of water discharged from oxidation means 36 has a suitable purified value while purification system 10 is in the purification mode. "Purified value," as that term is used herein, is the measure of the carbon content of water. Preferably, the purified value is in the range of between about one (1) and fifty (50) parts of carbon per billion. The purified water discharged from water purification system 10 is suitable for use as ultrapure water. "Ultrapure water," as that term is used herein, means water which has a TOC in the range of below about ten parts per billion and an electrical resistivity in the range of between about seventeen and 18.2 megohm-cm.

While purification system 10 is in the purification mode, the water is directed from water source 12 through purification system 10 at substantially steady-state conditions. "Steady-state conditions," as that term is used herein, means that the TOC of the water at water source 12, the nature of organic contaminant within the water at water source 12, and the flow rate and temperature of the water directed through purification system 10, are maintained at substantially constant values.

The electrical resistivity of the water in conduit 22 is measured with first resistivity cell 24. The water thereafter passes through oxidation means 36, wherein the organic carbon in the water oxidizes to form carbon dioxide and other oxidation products. The electrical resistivity of the water is then again measured, at second resistivity cell 44, as it is discharged from oxidation means 36 through outlet 40 and is directed through conduit 42.

The electrical resistivity of water is inversely related to the amount of carbon dioxide present in the water. Therefore, water which includes organic carbon which is oxidized in oxidation means 36 will have a lower electrical resistivity than the same water before treatment in oxidation means 36. Consequently, under substantially steady state conditions, the difference between the electrical resistivity of water passing through purification system 10 at first resistivity cell 24 and at second resistivity cell 44 will remain substantially constant. The purification-mode resistivity change is the difference in electrical resistivity between first and second resistivity cells 24,44 when purification system 10 is in the purification mode and at substantially steady-state conditions.

The purification-mode resistivity change is associated with the purified value of the water as it passes through purification system 10. For example, if the steady-state conditions of purification system 10 in the purification mode are disturbed, the TOC of water discharged from oxidation means 36 can vary significantly from the purified value obtained under the previous steady state conditions. Significant variation of the TOC of water discharged from oxidation means 36 will be associated by a significant change in electrical resistivity of water at first resistivity cell 24, second resistivity cell 44, or both. As a consequence, the purification-mode resistivity change, which is a measure of the difference between the measurements of electrical resistivity by first and second resistivity cells 24,44, will also change.

Water purification system 10 is then operated in a reference mode to obtain a first reference-mode resistivity change associated with the purified value of water discharged from water purification system 10 in the purification mode. Water purification system 10 is operated in the reference mode by first actuating three-way valve 26 from the first position to the second position. Water is thereby diverted from oxidation means 36 through second outlet 32 of three-way valve 26. Water which had previously been directed into oxidation means 36 consequently becomes trapped within oxidation means 36. The water in oxidation means 36 remains trapped and exposed to conditions sufficient to oxidize organic carbon components of the water, for a measured period of time.

Three-way valve 26 is then actuated from the second position to the first position, whereby water is rediverted from second outlet 32 through first outlet 30 of three-way valve 26 and through oxidation means 36, thereby flushing the previously trapped water from oxidation means 36 through outlet 40 and conduit 42. The electrical resistivity of the water which had been trapped in oxidation means 36 is then measured at second resistivity cell 44.

Three-way valve 26 is again actuated from the first position to the second position to divert water from oxidation means 36 through second outlet 32 to the effluent, thereby trapping a second volume of water within oxidation means 36 for continuous exposure to conditions sufficient to oxidize the organic carbon component of the water. The period of time during which the second volume of water is trapped within oxidation means 36 is significantly different than the period of time during which the first volume of water was trapped within oxidation means 36. Three-way valve 26 is then actuated from the second position back to the first position to flush the second volume of water from oxidation means 36 and through conduit 42 for measurement of the electrical resistivity of the second volume at second resistivity cell 44.

Three-way valve 26 is successively actuated to divert and then redivert water away from and then back through oxidation means 36 to thereby trap a sufficient number of volumes of water in oxidation means 36 for significantly different periods of time. This enables calculation of the change in electrical resistivity of the water upon oxidation in oxidation means 36 corresponding to an infinite period of time. Since the time periods during which different volumes of water are trapped in oxidation means 36 are significantly different, the measured electrical resistivity of the total number of trapped volumes can be employed collectively to calculate the difference of electrical resistivity of the water upon exposure to the oxidizing conditions within oxidizing means 36 for a period of time sufficient to cause the change of resistivity over time to become essentially zero, such as when the water has been exposed to oxidizing conditions for an infinite period of time. This difference in resistivity is determined by employing the values of electrical resistivity, obtained from the volumes of water trapped within oxidation means 36 while water purification system is in the reference mode, to calculate the electrical resistivity of the water when the second derivative of the change in electrical resistivity with respect to time is zero.

Preferably, about five different volumes of water are trapped in oxidation means 36 for significantly different periods of time. In a particularly preferred embodiment, the first through fifth volumes of water are trapped for twenty (20), thirty (30), forty (40), fifty (50) and sixty (60) seconds, respectively, in oxidation means 36.

The calculated first reference-mode resistivity change can be associated with the organic carbon content of water at the first resistivity cell, by employing, for example, a suitable computer modeling program. An example of a suitable computer modeling program is a "MINTEQA2" computer modeling program for modeling ionic equilibria in an aqueous media. The MINTEQA2 computer modeling program is disclosed in U.S. Environmental Protection Agency publication EPA/600/3-91/021 (1991), the teachings of which are incorporated herein by reference.

Purification system 10 is then returned to the purification mode by returning three-way valve 26 to the first position and reestablishing the steady-state conditions at which the purified value of the water was measured. In one embodiment, first and second resistivity cells 24,44 are employed continuously to obtain a continuous measurement of the difference in electrical resistivity of water directed through water purification system 10 at first and second resistivity cells 24,44 during purification of water to produce ultrapure water in the purification mode. Alternatively, first and second resistivity cells 24,44 can be employed intermittently to obtain values of the purification-mode resistivity change.

The organic carbon content, of water discharged from purification system 10 is predicted by combining the reference-mode resistivity change ($\Delta R_{rm}$) and the organic carbon content of water at the first resistivity cell ($OCC_1$), as estimated from $\Delta R_{rm}$ by the method described above, with the purification-mode resistivity change ($\Delta R_{pm}$). Preferably, the reference-mode resistivity change and the purification-mode resistivity change are combined to predict the organic carbon content ($OCC_2$) of water discharged from oxidation means 36 by employing the following formula:

$$OCC_2 = OCC_1 * (\Delta R_{rm}/\Delta R_{pm} - 1).$$

Optionally, additional calculations of the organic carbon content can be made by employing subsequent measurements of the purification-mode resistivity change in the above formula without returning to the reference mode if changes in the purifications-mode resistivity change are not significant. Water which has a suitable purified value as it is discharged from oxidation means 36 will be polished by polisher 46 at suitable steady-state conditions to ultrapure quality (i.e. resistivity). The resistivity of water discharged from polisher 46 can be measured with third resistivity cell 48 in order to check that the resistivity is within the expected range for that of ultrapure water.

Further, the purified value of water discharged from oxidation means 36 can be monitored by the method of the invention. For example, a substantially constant value of the purification-mode resistivity change over time indicates that steady-state conditions are being maintained within water purification system 10 and that water discharged from water purification system 10 is ultrapure. Therefore, a substantially constant value of the purification-mode resistivity change indicates, over at least a period of time, such as about a day, that the discharged water is ultrapure. However, water purification system 10 preferably is periodically returned, such as about once a day, to the reference-mode to determine a new value of the reference-mode resistivity change, so that the ultrapure quality of the water discharged from water purification system 10 can be verified.

Conversely, a significant variation of the purification-mode resistivity change indicates a disturbance in the steady-state conditions of water purification system 10 in the purification mode. Disturbance in the steady-state conditions can be caused, for example, by variation in temperature of water at water source 12, variation in the flow rate of water through water purification system 10, exhaustion of treatment elements in treatment means 16, fluctuation of the ultraviolet light emitted in oxidation means 36, variation in the concentration or type of organic components of water at water source 12, etc.

The parameters of water purification system 10 can be manipulated to return the electrical resistivities of water at first and second resistivity cells 24,44 to the values obtained while the purified value was measured. However, measurements of electrical resistivities at first and second resistivity cells 24,44, while water purification system 10 is in the purification mode, are not alone sufficient to indicate that water discharged from oxidation means 36 has the previously established purified value. Neither is it sufficient to assure that water discharged from water purification system 10 is ultrapure.

For example, if the steady-state conditions of the water directed through purification system 10 in the purification mode are disturbed by variation of the organic carbon components of water source 12, exposure of the water in oxidation means 36 to conditions sufficient to cause a significant portion of the organic carbon to oxidize can result in a different distribution and concentration of partially oxidized ionic species of the organic carbon component in water discharged from oxidation means. Consequently, a difference in electrical resistivity between first and second resistivity cells 24,44 can be obtained which is substantially the same as the difference measured for water having an acceptable purified value, and yet the water discharged from oxidation means 36 can have a purified value which is significantly different than that obtained prior to the disturbance.

However, if the steady-state conditions of water purification system 10 in the purification mode are disturbed, as indicated by a significant variation of the difference in electrical resistivity between first and second resistivity cells 24,44, the purified value of water discharged from water purification system 10 can be verified by converting water purification system 10 to the reference mode to obtain a second reference-mode resistivity change. The method for obtaining the second reference-mode resistivity change is identical to that described above for obtaining the first reference-mode resistivity change. The second reference-mode resistivity change reflects the organic carbon content of water at first resistivity cell 24. If the second reference-mode resistivity change is substantially equivalent to that of the first reference-mode resistivity change, and if the purification-mode resistivity change has returned to its original value, then the purified value of water discharged from oxidation means 36 following significant variation of the steady-state conditions in the purification mode has been verified.

Alternatively, water purification system 10 is converted back to the purification mode and a new purification-mode resistivity change is measured. The second reference-mode resistivity change and the new purification mode resistivity change are then combined by using the previously described formula, to again predict the organic carbon content of water discharged from water purification system 10. The purification-mode resistivity change can also be measured, continuously or intermittently, for continued monitoring of the organic carbon content of water discharged from water purification system 10.

Figure 2:
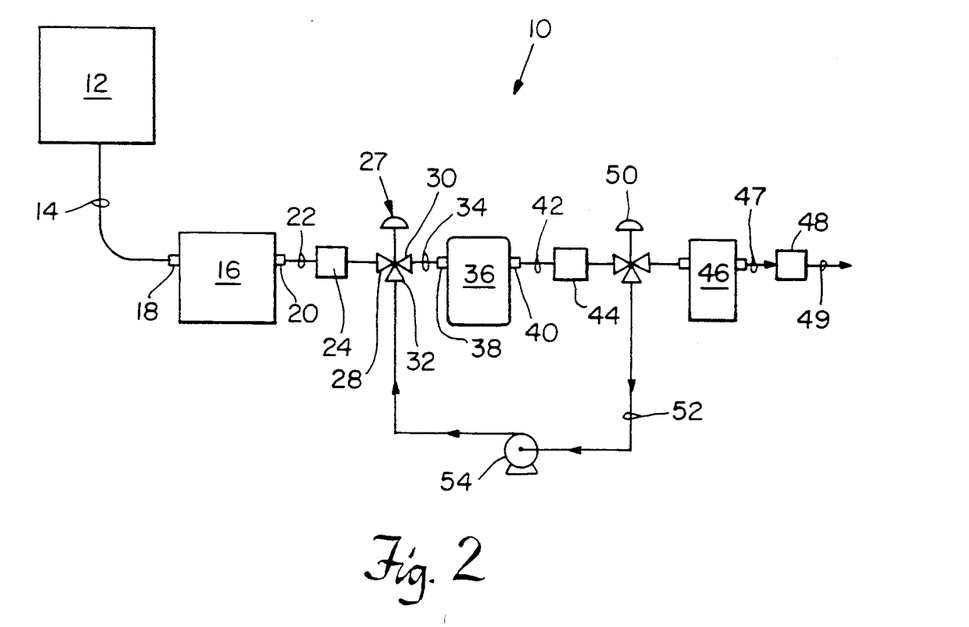
FIG. 2 is a schematic representation of another embodiment of the system of the invention.

In another embodiment, shown in FIG. 2, water purification system 10 includes three-way valve 50 at line 42. Recycle line 52 extends from three-way valve 50 to three-way valve 27. Pump 54 is disposed at recycle line 52. Water purification system 10 is shifted from the purification mode to the reference mode by activating both of three-way valves 27,50 from first positions to second positions and by activating pump 54, whereby water is recirculated from line 42, through recycle line 52 to line 34 and oxidation means 36. Water is thereby exposed to oxidation in oxidation means 36 for a period of time proportional to the length of time during which water purification system 10 is in the reference mode. Determination of the reference-mode resistivity change includes measuring the change in resistivity across oxidation means 36 until the rate of change over time becomes essentially zero, indicating that the organic carbon content of the water has been fully oxidized to carbon dioxide.

Three-way valves 27,50 can then be returned to their first positions to restore water purification system 10 to the purification mode. A purification-mode resistivity change is measured and the carbon-content of water discharged from oxidation means 36, while water purification system 10 is in the purification mode, can be predicted as described above. Also, the carbon content can be monitored by continuously or intermittently measuring the purification-mode resistivity change and by reestablishing the reference mode if a significant variation of the purification-mode resistivity change is observed.

Exemplification

The following is an example of the method used to predict TOC discharged from a water purification system according to the method of the invention. The water source was tap water from Bedford, MA. A Milli-Q ® UV Plus water purification system, commercially available from Millipore Corporation, Inc., was modified to include the proper apparatus to measure total organic carbon content. The water was treated by reverse osmosis prior to introduction to the water purification system.

A steady-state purification mode resistivity change ($\Delta R_{pm}$) was measured as 6.50 Megohm-cm. This was held constant for a period of over 5 minutes. The pre- and post- ultraviolet (UV) light resistivity measurements were 18.10 and 11.50 Megohm-cm, respectively. The purification-mode resistivity change was determined as the difference of these two measurements.

During the reference-mode resistivity change determination, the following resistivity changes were observed:

| Oxidation Time | Resistivity Change |
|---|---|
| 20 seconds | 8.62 Megohm-cm |
| 30 seconds | 9.12 Megohm-cm |
| 40 seconds | 9.43 Megohm-cm |
| 50 seconds | 9.65 Megohm-cm |
| 60 seconds | 9.79 Megohm-cm |

These values were made by diverting the water stream using a three-way valve before the UV light. The water remaining trapped within the oxidation means was held there for the different oxidation times. The water remaining in the UV light during the oxidation times flowed through the post-UV resistivity cell when the three-way valve was turned back to its purification mode position. This was done for each oxidation time. After the reference mode, the change in the purification mode resistivity went back to 6.50 Megohm-cm.

A nonlinear regression analysis of the data yielded the following equation:

$$\text{Resistivity Change} = 10.056 - 3.323 * \exp(-0.042 * \text{time})$$

Figure 3:
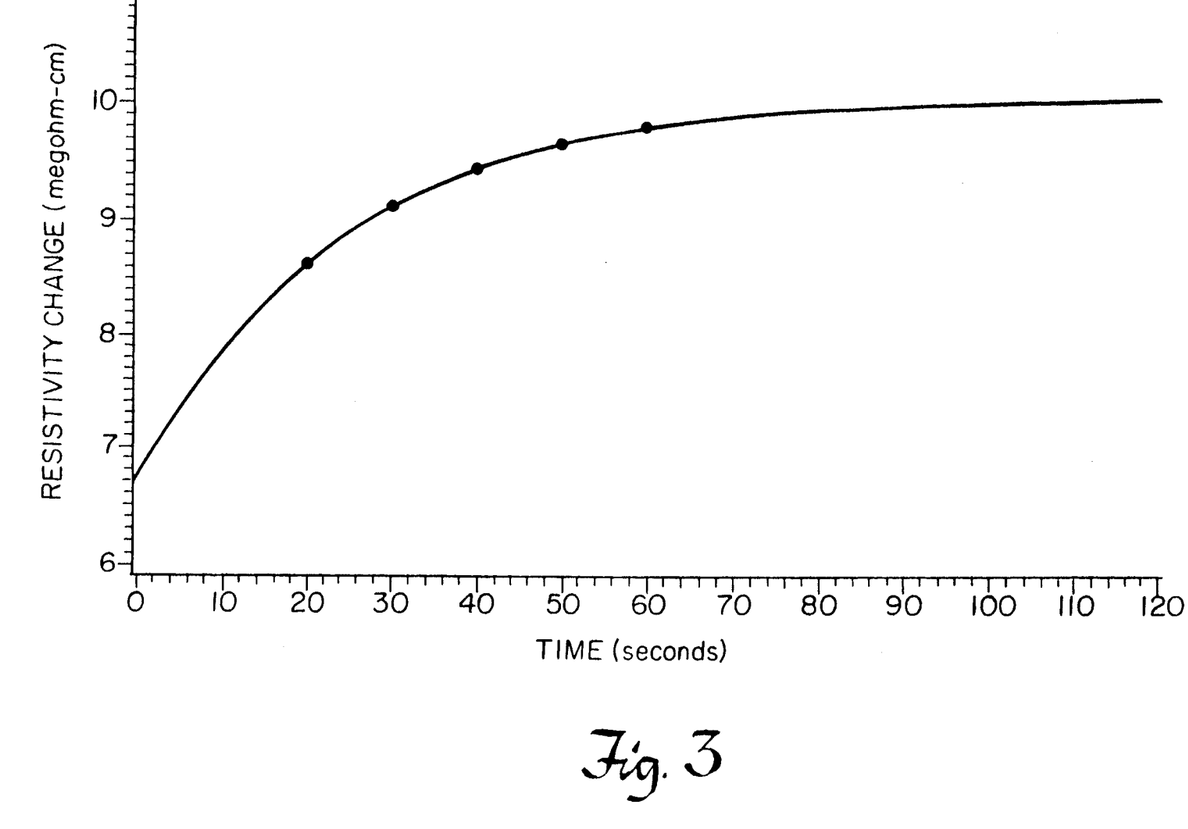
FIG. 3 is one example of a plot of the measured resistivity change of water during significant different time periods to allow calculation of a reference-mode resistivity change.

A plot of this equation is shown in FIG. 3. The calculated value at infinite time was 10.056 Megohm-cm, and was identified as the reference-mode resistivity change ($\Delta R_{rm}$). From $R = 18.10 - \Delta R_{rm}$, the value of R is 8.04 Megohm-cm.

The resistivity value at infinite time was a projected value from short time measurements and eliminated the effects of extractables. This was the resistivity change expected from total oxidation of the organic carbon in the water stream.

The complete oxidation of organic carbon yielded carbon dioxide ($CO_2$). The $CO_2$ dissolved in water to form a complex solution of different ionic species. Each of these species had a different specific resistivity/conductivity value associated with it.

A MINTEQA2 computer program (hereinafter "MINTEQA2") was used to convert the reference-mode resistivity change to an organic carbon content of water entering the UV light unit. When using MINTEQA2, we input a part-per-billion level of organic carbon to be fully oxidized to $CO_2$. MINTEQA2 predicted the concentration of aqueous species which resulted from this oxidation. These species included hydronium ($H^+$), hydroxide ($OH^-$), bicarbonate ($HCO_3^-$), and carbonate ($CO_3^{2-}$).

Figure 4:
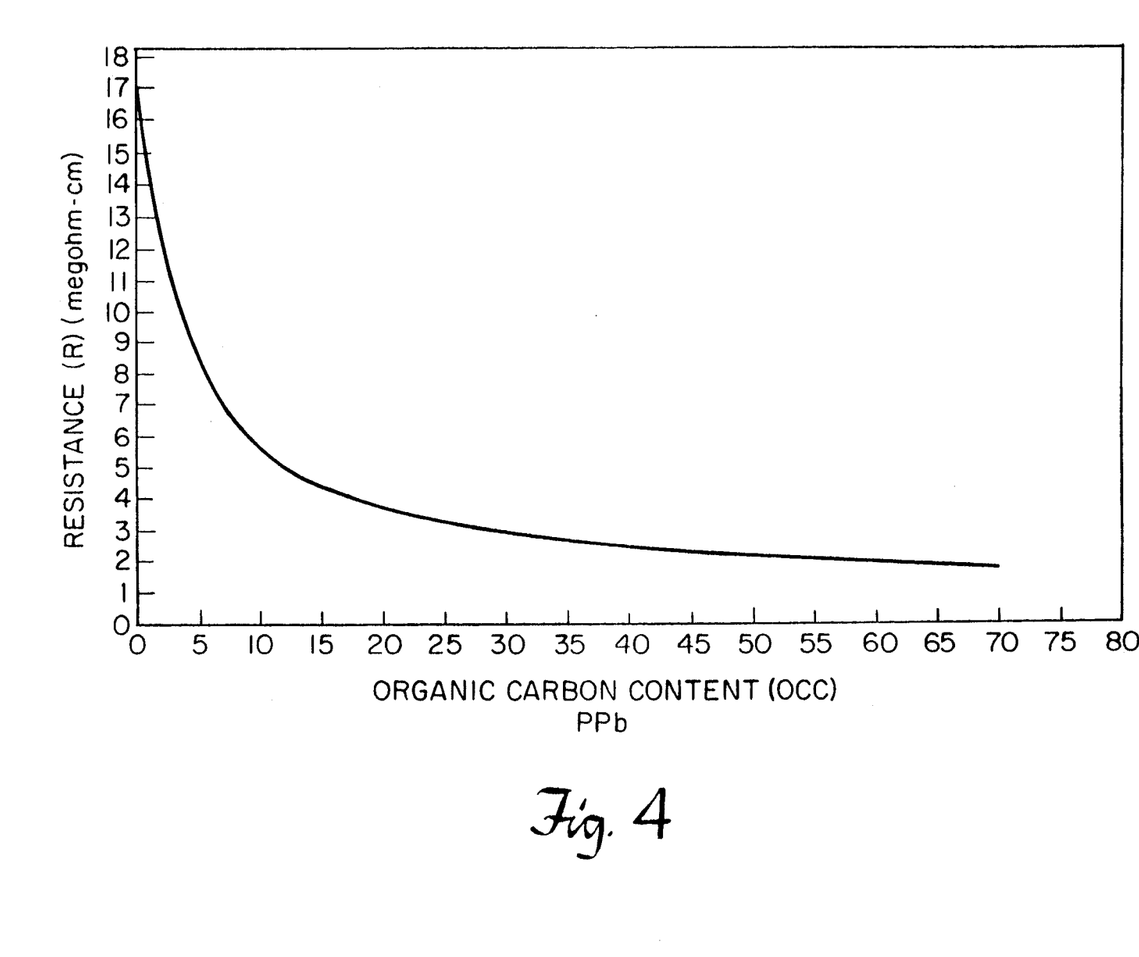
FIG. 4 is a plot of the organic carbon content of water versus the calculated resistivity of the water over an infinite oxidation time.
Figure 5:
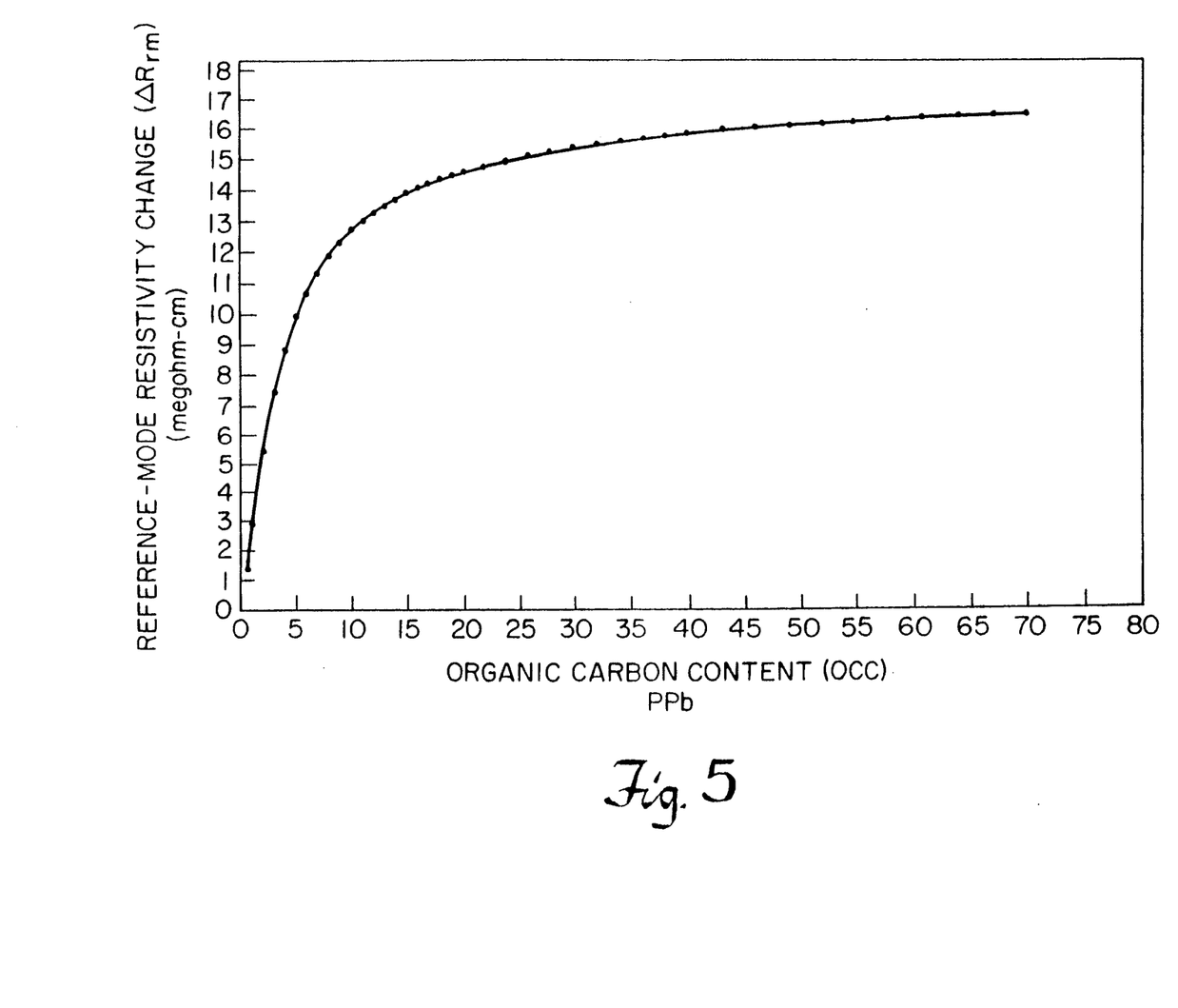
FIG. 5 is a plot of the organic carbon content of water versus the reference-mode resistivity change.

The calculated concentrations of these species from MINTEQA2 were multiplied by the specific conductance of each ion to determine the contribution to total conductivity by each ion. These conductivities were then added together to determine the total resistivity change the water. An equation was then derived from the results of the computer analysis. The equation is shown below:

$$OCC_1 = -2.3896 + 45.049/R + 133.78/R^2 + 35.202/R^3$$

where "$OCC_1$" is the calculated organic carbon content of the water just prior to introduction to the UV resistivity cell. A plot of this equation is shown in FIG. 4. Using 8.04 Megohm-cm as R yielded an $OCC_1$ of 5.35 ppb from the above equation. Alternatively, the determinations of R from the reference-mode resistivity change and of $OCC_1$ can be combined to obtain a single plot, which is shown in FIG. 5. For the purpose of comparison, a measurement of 5.28 ppb for the same water was made independently by using an Anatel SE-100 measuring device.

A mass balance model was developed for predicting the organic carbon content of water discharged from the water purification system ($OCC_2$) from values of $OCC_1$, the reference-mode resistivity change ($\Delta R_{rm}$) and the purification-mode resistivity change ($\Delta R_{rm}$).

The following equation was then employed:

$$OCC_2 = OCC_1 * (\Delta R_{rm}/\Delta R_{pm} - 1)$$

Using $OCC_1 = 5.35$ ppb, $\Delta R_{rm} = 10.056$ Megohm-cm, and $\Delta R_{pm} = 6.50$ Megohm-cm, $OCC_2$ was calculated to be 2.93 ppb. For the purpose of comparison, a measurement of organic carbon content of 2.92 ppb was made independently using an Anatel SE-100 measuring device.

Equivalents

Those skilled in the art will recognize, or be able to ascertain using no more than routine experimentation, many equivalents to specific embodiments of the invention described specifically herein. Such equivalents are intended to be encompassed in the scope of the following claims.

We claim:
1. A method for predicting the organic carbon content of water discharged from a water purification system, comprising the steps of:
   a) directing the water from a water source through an oxidation means of the water purification system under substantially steady-state conditions;
   b) establishing a reference mode by exposing water to the oxidation means for a predetermined number of substantially different time periods to determine a reference-mode resistivity change;
   c) establishing a purification mode, wherein the water is directed through the oxidation means under said steady-state conditions;
   d) measuring a purification-mode resistivity change of the water across the oxidation means while the water purification system is at said steady state conditions; and
   e) combining the reference-mode resistivity change with the purification-mode resistivity change to obtain a purified value which is associated with the carbon content of water discharged from the water purification system, thereby predicting the carbon content of water discharged from the water purification system.

2. The method of claim 1 further including the step of polishing said water in the purification mode.

3. The method of claim 2 wherein the reference mode is established by recycling the water through the oxidation means and wherein determination of the reference-mode resistivity change includes measuring the change in resistivity across the oxidation means until a rate of said change over time is about zero.

4. The method of claim 2 wherein the reference mode is established by diverting flow of water through the water purification system from the oxidation means, and then rediverting flow through the oxidation means over a predetermined number of substantially different time periods to measure changes in resistivity of the water statically held within said oxidation means during a period when the flow of water is diverted therefrom to determine the reference-mode resistivity change.

5. The method of claim 4 further including the step of measuring the resistivity of the water after the water has been polished in the purification mode of the water purification system.

6. The method of claim 5 wherein the step of directing water through the oxidation means includes exposing said water to ultraviolet light to cause the organic carbon content of the water to be reduced in the oxidation means to the purified value.

7. The method of claim 6 wherein the purification-mode resistivity change is measured by:
   a) measuring a first resistivity value of water before exposure of the water to ultraviolet light in the oxidation means;
   b) measuring a second resistivity value of water, after exposure of the water to ultraviolet light in the oxidation means; and
   c) subtracting the second resistivity value from the first resistivity value to obtain said purification-mode resistivity change of water across the oxidation means while the water purification system is in the purification mode and at substantially steady-state conditions.

8. The method of claim 7 wherein the water is diverted from the oxidation means and then rediverted through the oxidation means in the reference mode by actuating a three-way valve which is disposed at a conduit extending between a first resistivity cell, said first resistivity cell being employed to measure the first resistivity of water before exposure of the water to ultraviolet light, and said oxidation means, wherein said water is exposed to said ultraviolet light.

9. The method of claim 8 wherein the first reference mode resistivity change is determined by employing the resistivity changes measured in the reference mode during the different exposure times of the water to ultraviolet light in the oxidation means to calculate the resistivity change which corresponds to the organic carbon content of the water at the water source.

10. The method of claim 9 further including the step of filtering the water before measuring said first resistivity of the water.

11. The method of claim 10 further including the step of carbon-treating the water.

12. The method of claim 11 further including the step of exposing said water to ion exchange before measuring said first resistivity.

13. The method of claim 12 further including the step of exposing the water to reverse osmosis before filtering the water in the water purification system.

14. The method of claim 13 wherein the water is exposed to sufficient reverse osmosis to cause said feed water, after carbon filtration and ion exchange to have an organic carbon content of less than about 10 parts per billion and an electrical resistivity of about 18.2 megohms-cm.

15. The method of claim 14 wherein the periods of time between diversion of the water from the oxidation means and then rediversion through the oxidation means in the reference mode extend over progressively increased periods of time.

16. The method of claim 1, wherein the purification-mode resistivity change is measured whereby the organic carbon content of water discharged from the water purification system in the purification mode can be verified, following significant variation of the purification mode resistivity change, by redirecting water through the water purification system in the reference mode to obtain a second reference-mode resistivity change which can be combined with said purification-mode resistivity change following said significant variation, to predict the carbon content of the water discharged from the water purification system, thereby monitoring the organic carbon content of water discharged from the water purification system.

17. A method for monitoring the organic carbon content of water discharged from a water purification system, comprising the steps of:
  a) directing the water from a water source through an oxidation means of the water purification system under substantially steady state conditions;
  b) establishing a reference mode by exposing the water to oxidation means for a predetermined number of substantially different time periods to determine a reference-mode resistivity change;
  c) establishing a purification mode, wherein the water is directed through the oxidation means under said steady state conditions;
  d) measuring a purification-mode resistivity change of the water across the oxidation means while the water purification system is at said steady state conditions, said purification mode resistivity change and said reference-mode resistivity change being together associated with the carbon content of water discharged from the water purification system while the water purification system is in the purification mode, whereby the organic carbon content of water discharged from the water purification system in the purification mode can be verified, following variation of the purification mode resistivity change, by redirecting water through the water purification system in the reference mode to obtain a second reference-mode resistivity change which can be combined with said purification-mode resistivity change following said variation, to predict the carbon content of water discharged from the water purification system, thereby monitoring the organic carbon content of water discharged from the water purification system.

18. An apparatus for predicting the organic carbon content of water discharged from a water purification system, comprising:
  a) a first three-way valve having at least one inlet and at least one outlet, said three-way valve being moveable from a first position, wherein water can be conducted from a water source through the valve and to an oxidation means, to a second position, wherein water is prevented from being conducted from the water source to said oxidation means;
  b) a first resistivity cell in fluid communication with an inlet of the first three-way valve;
  c) an oxidation means for exposing water directed through the purification system to conditions sufficient to oxidize the carbon content of the water to a purified value, the oxidation means having
    i) an inlet in fluid communication with an outlet of the first three-way valve, and
    ii) an outlet; and
  d) a second resistivity cell in fluid communication with the outlet of the oxidation means.

19. The apparatus of claim 18, further including a polishing means which is in fluid communication with the second resistivity cell, whereby water directed through said second resistivity cell is thereafter polished in said polishing means.

20. The apparatus of claim 19 wherein said oxidation means includes an ultraviolet light.

21. The apparatus of claim 20, further including a means for carbon-treating the water.

22. The apparatus of claim 21, further including a water treatment means which is in fluid communication with said first resistivity cell, wherein said treatment means partially purifies the water before the water is directed through said first resistivity cell.

23. The apparatus of claim 22 further including filtration means which includes an ion exchange resin.

24. The apparatus of claim 23, further including a third resistivity cell in fluid communication with an outlet of said polisher.

25. The apparatus of claim 24, further including:
  a) a second three-way valve disposed between the second resistivity cell and the polishing means;
  b) a recycle line disposed between the second three-way valve and the first three-way valve; and
  c) a pump disposed at the recycle line for recycling water in a reference mode from the second three-way valve through the recycle line and the first three-way valve to the oxidation means.

* * * * *